United States Patent [19]

Alfranca

[11] Patent Number: 4,729,374
[45] Date of Patent: Mar. 8, 1988

[54] SURGICAL INSTRUMENT FOR TRANSCHOLEDOCHAL PAPILLOTOMY

[76] Inventor: Jose-Maria P. Alfranca, Santa Tereas, 29-35, escalera 1ª-6º A, 50006 Zaragoza, Spain

[21] Appl. No.: 748,013

[22] Filed: Jun. 24, 1985

[30] Foreign Application Priority Data

Jun. 28, 1984 [ES] Spain ............................. 280274

[51] Int. Cl.⁴ .............................................. A61B 17/32
[52] U.S. Cl. .................................................. 128/305
[58] Field of Search ............ 128/305, 311, 312, 305.1, 128/305.3; 30/188, 189, 191, 246, 249, 250, 251

[56] References Cited

U.S. PATENT DOCUMENTS

| 279,413 | 6/1883 | McWilliams | 30/251 |
| 2,541,246 | 2/1951 | Held | 128/305 |
| 3,455,305 | 7/1969 | Ransy | 128/305 |

FOREIGN PATENT DOCUMENTS

| 0119405 | 9/1984 | European Pat. Off. | 128/305 |
| 2904115 | 8/1980 | Fed. Rep. of Germany | 128/305 |
| 715557 | 9/1931 | France | 30/251 |
| 548303 | 9/1956 | Italy | 128/305 |

*Primary Examiner*—Robert P. Swiatek
*Assistant Examiner*—David L. Tarnoff
*Attorney, Agent, or Firm*—Ladas & Parry

[57] ABSTRACT

A surgical instrument suitable for use in transcholedochal papillotomy for incision of duodenal papilla without duodenal incision is disclosed, comprising a fixed handle; a ring movably attached to the fixed handle; a transmission catheter suitable for insertion through a choledochus without duodenal incision, attached at one end to the fixed handle; a guide positioned within the transmission catheter and actuated by movement of a ring; a fixed blade attached at a second end of the transmission catheter, the fixed blade having a blunt distal end; a movable blade distally hinged to the fixed blade and closing thereon proximally and completely in a direction opposite to that of insertion, the movable blade being actuated by a guide; and a spring for displacing the control means back to an original position after movement therefrom, the original position corresponding to a closed position of the movable blade relative to the fixed blade.

11 Claims, 11 Drawing Figures

SURGICAL INSTRUMENT FOR TRANSCHOLEDOCHAL PAPILLOTOMY

BACKGROUND OF THE INVENTION

Currently a scissors having conventionally functioning cutting blades adapted to the small size of the papilla of Vater is employed to perform surgical or operative papillotomy. To perform this operation, it is necessary to incise the duodenum, manipulation taking place therethrough (transduodenal papillotomy).

OBJECT OF THE INVENTION

The instrument of the invention is inserted through the choledochus (transcholedochal papillotomy) without having to make an incision in the duodenum, thereby avoiding the serious risks of illness or death associated with duodenotomy taking place at present.

The scissors having an inverted cut constituting the instrument for performing papillotomy comprises a ring control which can be any mechanical or hydraulic means producing a movement capable of being transmitted. The ring control of this invention comprises two parts, one of which is fixed to a central ring and the other is movable, sliding on the former and provided with two lateral rings. The sliding of this part causes a guide to be introduced in the cylinder joined to the fixed part. A spring permanently maintains the instrument in a closed position.

The intermediate part of the instrument is comprised of a transmission catheter, wherefore it can effect the transmission mechanically or hydraulically. There is described a mechanical transmission which can, in turn, be rigid, flexible or malleable, and can have two parts, an outer fixed part joined to the cylindrical, hollow, rigid or malleable fixed blade of the control, and an inner slidable part constituting a movabable guide. The length of the catheter depends on the technique to be used; thus if insertion is carried out transcholedochally, which is the most direct route, the catheter would have to be shorter than if insertion were to be carried out through a much longer route, varying from about 10 to about 50 cm.

The head comprises two blades, one of which is fixed and is joined to the end of the transmission catheter. This fixed blade has a cylindrical shape, but it can be straight or curved, with a blunt distal end. It has an internal light for the passage of the movable guide of the transmission catheter and a recess for receiving the second or movable blade, as well as a transverse passage to engage therewith. The movable blade is distally hinged to the fixed blade, closing itself thereon proximally and completely. It has, above the articulation, a projection so that it can be hinged to the movable guide either directly or by means of a connecting-rod.

DETAILED DESCRIPTION OF THE INVENTION

Figure 1:
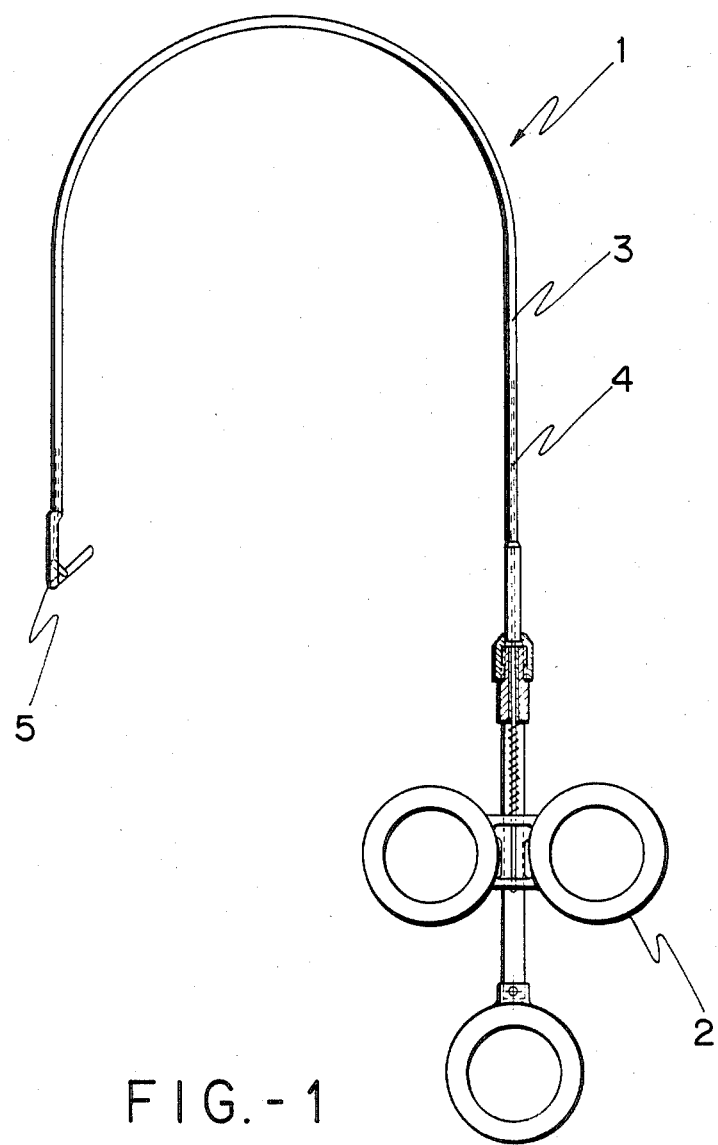
FIG. 1 shows a plan view of the instrument of the invention, illustrating its constitutive parts.
Figure 2:
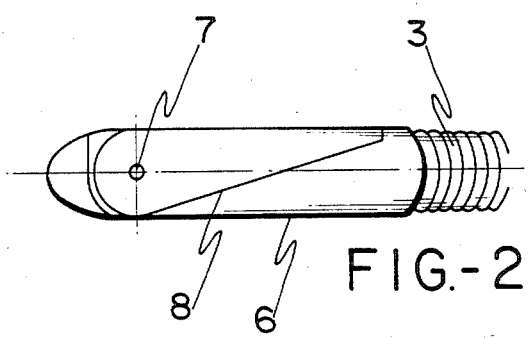
FIGS. 2 and 3 show heads of the instrument, one of them being straight and the other curved. The length and thickness both of the straight and the curved heads are variable, these latter being capable of adopting various radii of curvature.
Figure 3:
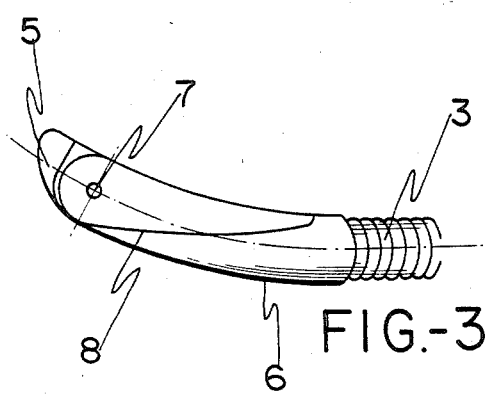

The instrument 1 of the invention comprises a ring control 2, a catheter 3 with the guide 4 positioned therein, and the head 5 comprising two blades, one of which is fixed and secured to the end of the catheter and the other movable and hinged to the fixed blade.

One of the ends of the catheter 3 is fixed to the ring control 2, whilst to its other end there is securely attached the fixed blade 6 on which, by means of the shaft 7, the movable blade 8 of of the head hinges.

Figure 4A:
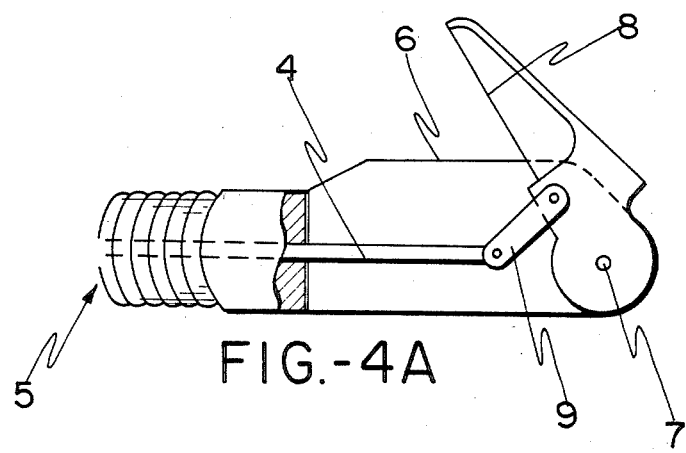
FIGS. 4A and 4B show the joining, by means of a connecting-rod, of the guide to the movable blade of the scissors, and illustrate the movable blade in an open and a closed position.
Figure 4B:
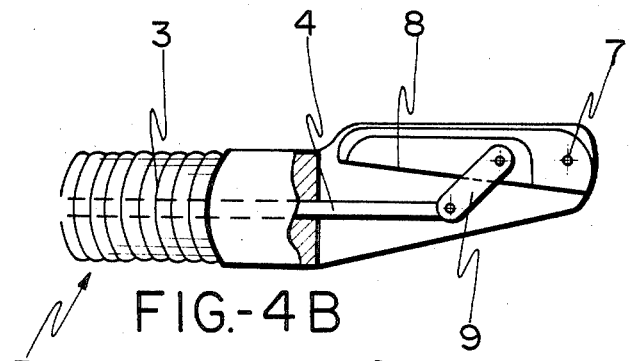
Figure 5A:
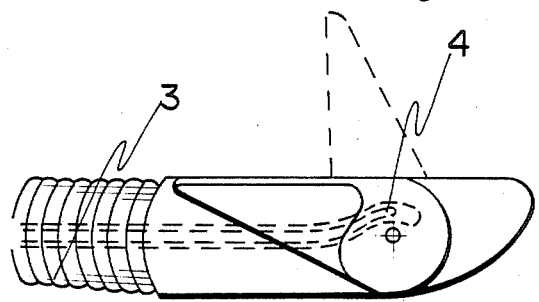
FIGS. 5A and 5B show the direct joining of the guide to the movable blade of the scissors, and illustrate two views of the head, in one of which the open position of the movable head is marked with dotted lines.
Figure 5B:
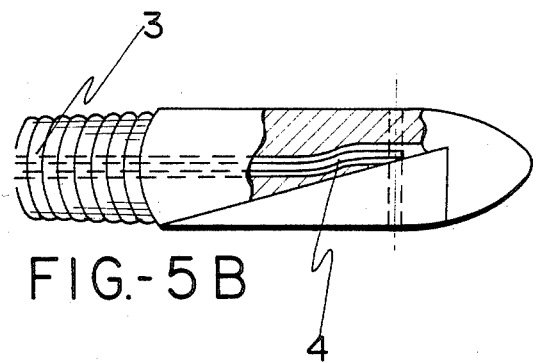
Figure 6A:
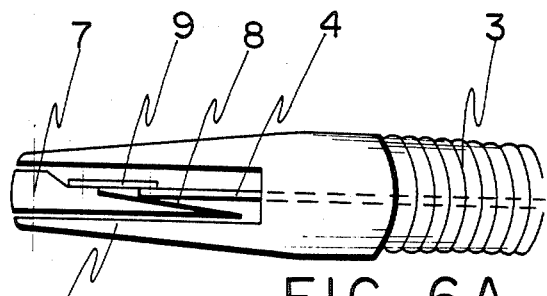
FIGS. 6A and 6B as well as 6C show an embodiment in which the movable blade is positioned between the fixed blade and a flange placed at the other side.
Figure 6B:
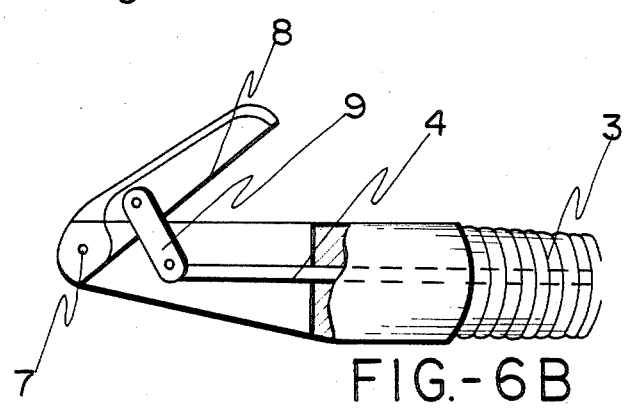
Figure 6C:
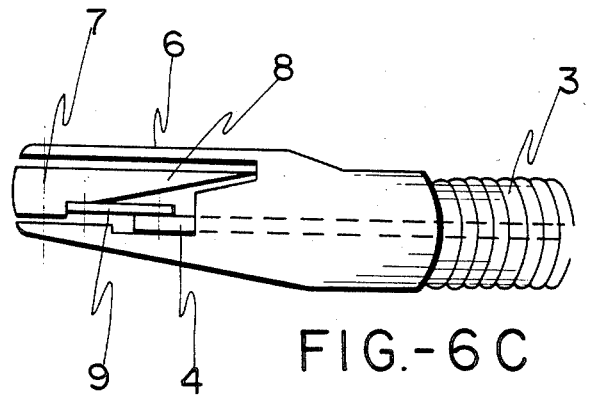
Figure 7:
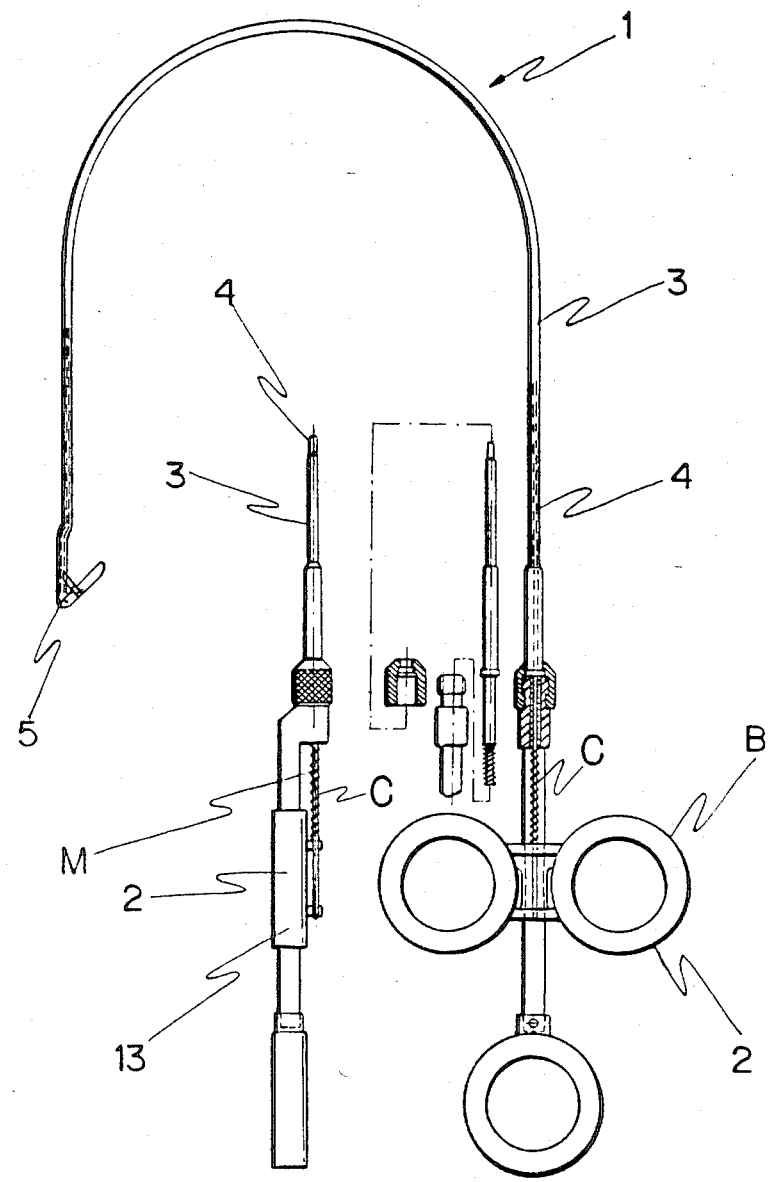
FIG. 7 shows an exploded view of the ring control.

The guide 4, by means of which the movable blade 8 is actuated, can be joined to it either directly or through a connecting-rod 9, as illustrated in FIG. 4.

When operating the ring control 2, the guide 4 is displaced causing the movable blade, to which it is joined, to open. However, since the spring of the ring control causes the guide to be displaced to its original position, the movable blade is closed again.

Functioning is as follows: Once the decision has been taken to perform papillotomy, longitudinal supraduodenal choledochtomy is practised, wherefore a thorough Kocher manipulation is not necessary. The catheter is inserted with the blade closed and facing downwards. The site of the blade is calculated, so that by maintaining the instrument in a position perpendicular to the bile duct, the blade will adopt the correct position, that is following the ascending direction of the smallest curvature of the duodenum. With a combined manipulation, the duodenum is touched to verify the passage of the head therein. At this moment the movable blade of the scissors is opened and by duodenal touching it can likewise be verified if it is in the correct position. The instrument is withdrawn until the scissors grips the papilla, at which moment the scissors is closed and without moving this position it is removed by choledochetomy. Papillotomy would have taken place depending on the size of the selected scissors.

If canalization of the papilla is not possible, then a smaller sized head must be used, or a head having a more closed curve, or a conventional dilator.

After papillotomy has been performed and by transcholedochal endoscopy, the presence and intensity of a possible hemorrhage must be verified. In the normal case of moderate or minimum hemorrhage, spontaneous hemostasis can be expected within a few minutes. If the hemorrhage persists or if it is massive, a balloon catheter will be inserted in the bile duct, which balloon swells in the duodenum and pulls it for five minutes. If, thereafter hemorrhage persists (exceptional case), the duodenum will be incised and hemostatis will be carried out under direct vision.

The choledochus will then be closed either directly or through internal drainage (transduodenocholedochal or through an outer T-catheter).

In favourable cases, the instrument can be inserted transcystico-choledochally, repeating the steps of the prior art, but terminating with mere ligature of the cystic duct.

With the instrument of the invention it is possible to perform, for the first time, a controlled papillotomy transcholedochally, the size of which depends on the requirements of the surgeon and on the patient's pathology.

Likewise, in particular cases (favourable), it can be performed transcystico-choledochally without having to incise the choledochus.

Use of the inventive device provides other advantages, such as the papillotomy technique is more rapid, easy and accessible to any surgeon under any conditions, whilst avoiding illness or mortality associated with duodenotomy.

In the event a "T" catheter has been used and there is residual pathology, an attempt could be made to insert a long thin model transfistularly 4–6 weeks thereafter to proceed with retrograde transfistulocholedochal papillotomy.

In exceptional cases, the device could be used transparieto-hepato-choledochally, or in any other application in which the distal end of a duct must be incised therethrough.

The control 2 operates by means of two pieces A and B. The piece A, serving as a support, is fixed and is in turn securely joined to the guide 4 of the other movable piece B sliding on the former, transmitting its movement to the catheter 3 inside which the guide 4 slides, attaining opening and closing of the movable blade of the scissors 5.

Piece B has a stud C securely joined to it, at one of the ends of which it is joined to the catheter 3 transmitting to it the movement upon displacement of piece B. The said piece B is urged by the action of the spring M in which there moves the stud C which forces the scissors to be maintained in the closed position.

Pieces A and B are provided with rings which serve to facilitate its mobilization with a single hand.

The head 5 is applicable to incise the papilla of vater during a surgical operation or an outer canalization of the bile duct.

I claim:

1. A surgical instrument suitable for use in transcholedochal papillotomy for incision of duodenal papilla without duodenal incision, comprising a fixed handle; control means movably attached to said fixed handle; a transmission catheter suitable for insertion through a choledochus without duodenal incision, attached at one end to said fixed handle; guide means positioned within said transmission catheter and actuated by movement of said control means; a fixed blade attached at a second end of said transmission catheter, said fixed blade having a blunt distal end; a movable blade distally hinged to said fixed blade and closing thereon proximally and completely in a direction opposite to that of insertion, said movable blade being connected to said guide means at a point between the hinge and a cutting line of said fixed and said movable blades, said movable blade being actuated by said guide means; and means for displacing said control means back to an original position after movement therefrom, said original position corresponding to a closed position of said movable blade relative to said fixed blade, whereby movement of said control means is transmitted by said guide means to said movable blade causing movement thereof from said closed position to an open position, after which said means for displacing said control means returns said control means to said original position, thereby actuating said guide means to return said movable blade to said closed position.

2. A surgical instrument according to claim 1, wherein said fixed blade has a cylindrical shape.

3. A surgical instrument according to claim 1, wherein said fixed blade is straight.

4. A surgical device according to claim 1, wherein said fixed blade is curved.

5. A surgical device according to claim 1, wherein said movable blade is directly connected to said guide means.

6. A surgical instrument according to claim 1, wherein said movable blade is connected to said guide means via a connecting rod.

7. A surgical instrument according to claim 1, wherein said fixed handle includes a ring to facilitate manipulation.

8. A surgical instrument according to claim 1, wherein said control means is provided with rings to facilitate manipulation.

9. A surgical instrument according to claim 1, wherein said means for displacing said control means back to an original position comprises a spring.

10. A surgical instrument according to claim 1, wherein said fixed handle further comprises a cylinder within which said guide means moves when actuated by movement of said control means.

11. A surgical instrument according to claim 1, wherein said fixed blade has a recess for receiving said movable blade.

* * * * *